US011903610B2

(12) United States Patent
Pilgeram et al.

(10) Patent No.: US 11,903,610 B2
(45) Date of Patent: Feb. 20, 2024

(54) SURGICAL CANNULA AND METHODS OF USE

(71) Applicant: Stryker Corporation, Kalamazoo, MI (US)

(72) Inventors: Kyle Craig Pilgeram, San Jose, CA (US); Ross Callison, Denver, CO (US)

(73) Assignee: Stryker Corporation, Kalamazoo, MI (US)

( * ) Notice: Subject to any disclaimer, the term of this patent is extended or adjusted under 35 U.S.C. 154(b) by 64 days.

(21) Appl. No.: 17/519,131

(22) Filed: Nov. 4, 2021

(65) Prior Publication Data

US 2022/0054165 A1 Feb. 24, 2022

Related U.S. Application Data

(63) Continuation of application No. 16/270,353, filed on Feb. 7, 2019, now Pat. No. 11,172,957.

(60) Provisional application No. 62/627,475, filed on Feb. 7, 2018.

(51) Int. Cl.
| | |
|---|---|
| *A61B 17/34* | (2006.01) |
| *A61B 17/02* | (2006.01) |
| *A61B 1/317* | (2006.01) |
| *A61B 17/32* | (2006.01) |

(52) U.S. Cl.
CPC .......... *A61B 17/3421* (2013.01); *A61B 17/02* (2013.01); *A61B 17/3423* (2013.01); *A61B 17/3431* (2013.01); *A61B 1/317* (2013.01); *A61B 17/320016* (2013.01); *A61B 2017/3429* (2013.01); *A61B 2017/3484* (2013.01)

(58) Field of Classification Search
CPC ............ A61B 17/3431; A61B 17/3429; A61B 17/3433; A61B 17/3421
See application file for complete search history.

(56) References Cited

U.S. PATENT DOCUMENTS

| | | | |
|---|---|---|---|
| 3,856,021 A | 12/1974 | McIntosh | |
| 3,970,090 A | 7/1976 | Loiacono | |
| 4,418,693 A | 12/1983 | LeVeen et al. | |
| 4,809,679 A | 3/1989 | Shimonaka et al. | |
| 5,002,557 A | 3/1991 | Hasson | |
| 5,058,580 A | 10/1991 | Hazard | |
| 5,545,179 A | 8/1996 | Williamson, IV | |

(Continued)

FOREIGN PATENT DOCUMENTS

| | | |
|---|---|---|
| DE | 3002298 A1 | 7/1981 |
| EP | 2044889 A1 | 4/2009 |
| KR | 20070026472 A | 3/2007 |

OTHER PUBLICATIONS

Arthrex PassPort Button Cannula™ Brochure, 2011, Arthrex Inc., LB0195C.

(Continued)

*Primary Examiner* — Julianna N Harvey
(74) *Attorney, Agent, or Firm* — Lerner David LLP

(57) ABSTRACT

A cannula comprising a monolithic, flexible body having a central passageway bounded by a first flange and a second flange, the central passageway having an irregular shape and a diaphragm positioned therein, the first diaphragm having the same irregular shape and including at least one first diaphragm slit, and a second diaphragm positioned adjacent to or at one of the first or second flanges and having at least one second diaphragm slit.

20 Claims, 17 Drawing Sheets

(56) References Cited

U.S. PATENT DOCUMENTS

| | | |
|---|---|---|
| 5,588,949 A | 12/1996 | Taylor et al. |
| 5,814,058 A | 9/1998 | Carlson et al. |
| 5,830,191 A * | 11/1998 | Hildwein ............... A61B 17/29 |
| | | 411/502 |
| 5,916,198 A | 6/1999 | Dillow |
| 6,033,426 A | 3/2000 | Kaji |
| 6,168,607 B1 | 1/2001 | Wattiez et al. |
| 6,171,282 B1 * | 1/2001 | Ragsdale ........... A61B 17/3423 |
| | | 604/164.11 |
| 6,276,661 B1 | 8/2001 | Laird |
| 6,589,264 B1 | 7/2003 | Barbut et al. |
| 6,749,601 B2 | 6/2004 | Chin |
| 6,793,621 B2 | 9/2004 | Butler et al. |
| 6,808,492 B2 | 10/2004 | Snyder |
| 7,255,687 B2 | 8/2007 | Huang et al. |
| 7,377,897 B1 | 5/2008 | Kunkel et al. |
| 7,413,542 B2 | 8/2008 | Kucklick et al. |
| 7,445,596 B2 | 11/2008 | Kucklick et al. |
| 8,012,083 B2 | 9/2011 | Kucklick et al. |
| 8,038,652 B2 | 10/2011 | Morrison et al. |
| 8,043,319 B2 | 10/2011 | Lyon et al. |
| 8,128,601 B2 | 3/2012 | Kunkel et al. |
| 8,157,833 B2 | 4/2012 | Au et al. |
| 8,231,570 B2 | 7/2012 | Ortiz et al. |
| 8,298,185 B2 | 10/2012 | Worrel et al. |
| 8,328,716 B2 | 12/2012 | Schmieding et al. |
| 8,353,873 B2 | 1/2013 | Sakai, Jr. et al. |
| 8,435,174 B2 | 5/2013 | Cropper et al. |
| 8,474,459 B2 | 7/2013 | Schnell |
| 8,753,267 B2 | 6/2014 | Stopek |
| 8,764,647 B2 | 7/2014 | Kleyman |
| 8,777,902 B2 | 7/2014 | Worrel et al. |
| D712,033 S | 8/2014 | Richard et al. |
| 8,795,235 B2 | 8/2014 | Mastri et al. |
| 8,814,780 B2 | 8/2014 | Kucklick et al. |
| 8,932,214 B2 | 1/2015 | Hart et al. |
| 9,089,363 B2 | 7/2015 | Dooney, Jr. et al. |
| 9,113,951 B2 | 8/2015 | Richard et al. |
| D738,500 S | 9/2015 | Richard et al. |
| 9,119,663 B2 | 9/2015 | Webb |
| 9,149,294 B2 | 10/2015 | Webb |
| 9,161,747 B2 | 10/2015 | Whittaker et al. |
| 9,271,639 B2 | 3/2016 | Cruz et al. |
| 9,314,269 B2 | 4/2016 | Webb et al. |
| 9,398,924 B2 | 7/2016 | Webb |
| 9,675,379 B2 | 6/2017 | Kucklick |
| 9,808,282 B2 | 11/2017 | Spenciner |
| 9,833,260 B2 | 12/2017 | Jolly et al. |
| 9,867,706 B2 | 1/2018 | Bonutti |
| 2005/0043682 A1 | 2/2005 | Kucklick et al. |
| 2005/0216027 A1 | 9/2005 | Suh et al. |
| 2006/0006931 A1 | 1/2006 | Hsieh et al. |
| 2006/0069391 A1 | 3/2006 | Jackson |
| 2006/0216027 A1 | 9/2006 | Izumi |
| 2007/0026472 A1 | 2/2007 | Prokash et al. |
| 2008/0108875 A1 | 5/2008 | Kunkel et al. |
| 2008/0109038 A1 | 5/2008 | Steiner et al. |
| 2008/0242930 A1 | 10/2008 | Hanypsiak et al. |
| 2009/0204081 A1 | 8/2009 | Whittaker et al. |
| 2009/0221968 A1 * | 9/2009 | Morrison ........... A61B 17/3423 |
| | | 604/164.11 |
| 2009/0326332 A1 * | 12/2009 | Carter ................ A61B 17/3423 |
| | | 600/235 |
| 2010/0168674 A1 | 7/2010 | Shaw et al. |
| 2010/0286484 A1 * | 11/2010 | Stellon ................ A61M 13/003 |
| | | 600/206 |
| 2012/0116459 A1 | 5/2012 | Nottmeier |
| 2012/0157782 A1 * | 6/2012 | Alfieri ................ A61B 17/3423 |
| | | 600/206 |
| 2012/0245426 A1 | 9/2012 | Salvas et al. |
| 2012/0253376 A1 | 10/2012 | Liu et al. |
| 2012/0277541 A1 * | 11/2012 | Bhargava .......... A61M 39/0247 |
| | | 604/164.11 |
| 2012/0323061 A1 | 12/2012 | Stalons |
| 2012/0323081 A1 | 12/2012 | Son |
| 2013/0303858 A1 | 11/2013 | Whittaker et al. |
| 2014/0022863 A1 | 1/2014 | Christie |
| 2014/0114367 A1 * | 4/2014 | Jolly .................. A61B 17/1764 |
| | | 606/86 R |
| 2015/0216562 A1 * | 8/2015 | Norton ............... A61B 17/0218 |
| | | 600/204 |
| 2017/0273717 A1 | 9/2017 | Kucklick |

OTHER PUBLICATIONS

ConMed Cannula Portfolio, 2015, CONMED Corporation, M2015217 11/15.

* cited by examiner

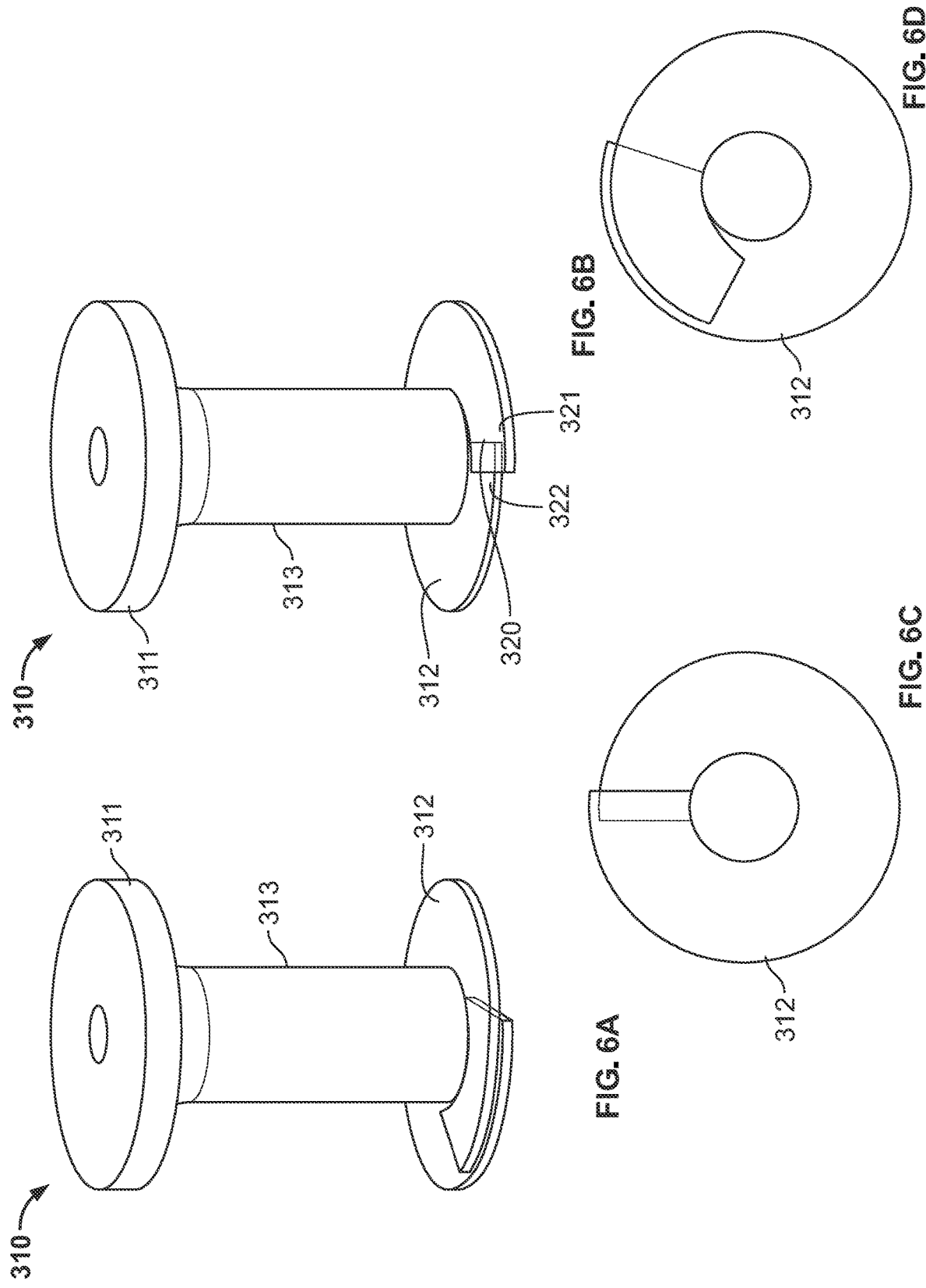

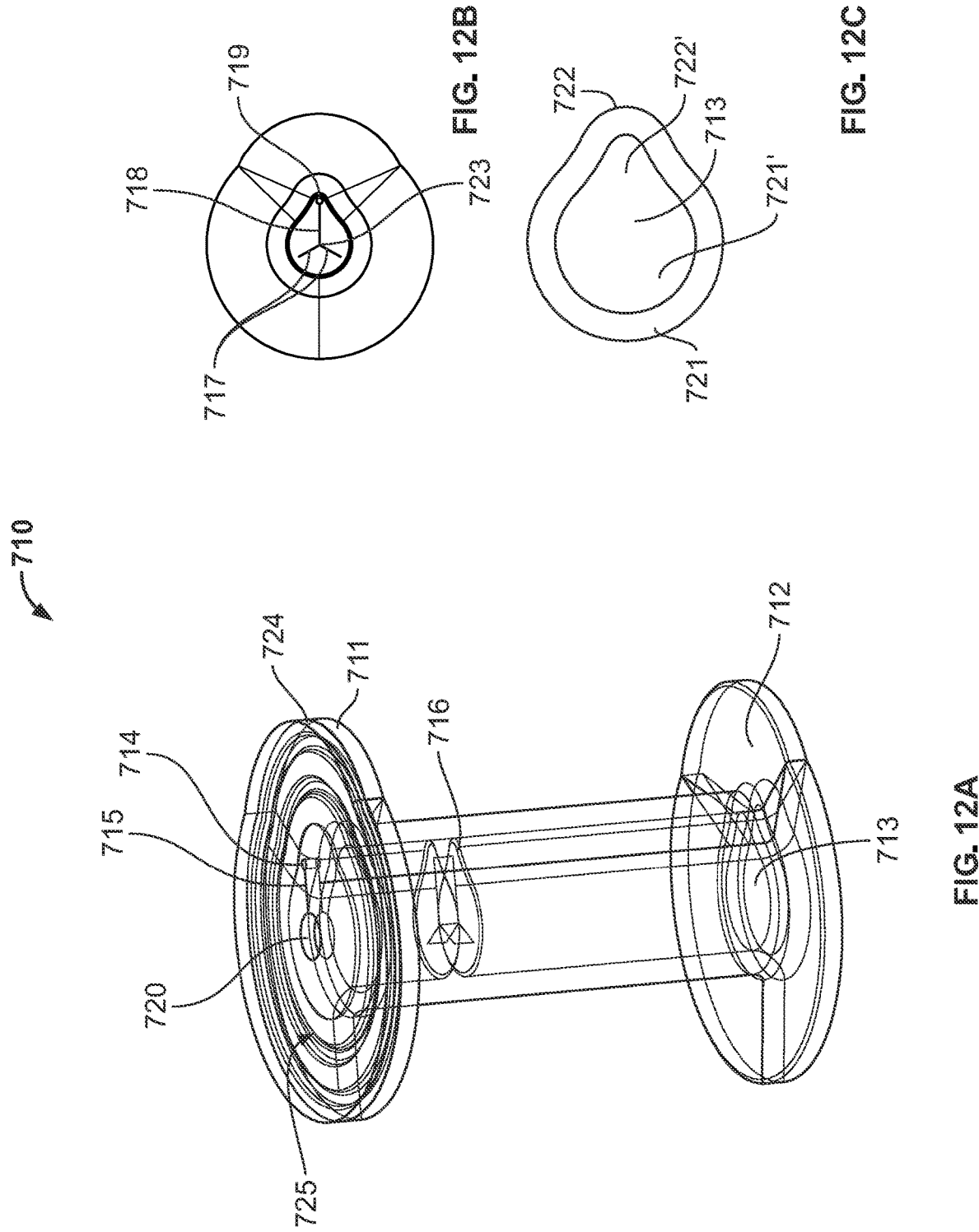

SURGICAL CANNULA AND METHODS OF USE

CROSS-REFERENCE TO RELATED APPLICATIONS

This application is a continuation of U.S. application Ser. No. 16/270,353, filed on Feb. 7, 2019, which application claims the benefit of the filing date of U.S. Provisional Patent Application No. 62/627,475 filed Feb. 7, 2018, the disclosure of which is hereby incorporated herein by reference.

BACKGROUND OF THE INVENTION

Surgical cannulas are ubiquitous to arthroscopy. Such cannulas provide access to internal anatomy via a minimally invasive opening through the cutaneous and subcutaneous tissues and, in no uncertain terms, make arthroscopic surgeries possible.

Oftentimes, the most difficult part of using a surgical cannula is inserting it into the patient. Rigid cannulas can be difficult to pass through the surgical opening, potentially requiring a larger opening to allow passage of a flange or other structure intended to ultimately anchor the cannula to the tissue and the patient. Also, rigid cannulas can sometimes prevent a large jawed instrument from opening fully if the jaws are in a position to interact with the rigid distal end of the cannula.

In order to overcome some of the shortcomings of these rigid cannulas, flexible or pliable cannulas have been developed. These flexible cannulas, on the other hand, can be difficult to stabilize once passed through the surgical opening. In particular, typical flexible cannulas can be difficult to "catch" onto the tissue, which is necessary for the operator to know when the cannula is through the tissue and is ready to be released. Instead, typical flexible cannulas lack adequate structure which can provide the tactile feedback that would be helpful to understand the positioning of the cannula within the patient during placement. For example, when inserting such a cannula into the shoulder joint for performing rotator cuff surgery, the operator will grasp the distal flange of the cannula with a hemostat by folding the flange in half and clenching down on it with the hemostat jaws. However, the resulting shape of the distal flange is inadequate in many ways. Most importantly, the resulting shape makes it difficult for the operator to know when the distal end of the cannula has passed through the tissue layers, passed the interior tissue wall, and entered the joint space since it does not have a reliable shape with a useful projection or "catch" surface of material that can engage the interior tissue wall.

Thus, there exists a need in the art for a cannula that is flexible, to allow for passage through a small surgical opening in tissue, while having an area of sufficient rigidity or substance that can "catch" onto tissue and provide affirmative tactile feedback to the operator that the cannula is in a proper position, and further, that provides a user with adequate usability once the cannula is in place.

BRIEF SUMMARY OF THE INVENTION

The present disclosure is directed to a cannula for surgical applications, particularly arthroscopic surgical procedures. For example, the cannula may be used for orthopedic arthroscopic surgeries, such as rotator cuff repair, shoulder instability, knee surgeries (e.g., ligament or soft tissue repair), hip surgeries (e.g., femoroacetabular impingement, soft tissue and instability repairs), and the like.

In one embodiment, a cannula includes a monolithic, flexible body having a central passageway bounded by a first flange and a second flange, the first flange being generally circular, the central passageway being generally cylindrical along its length, and the second flange having an irregular shape. Further, the second flange may include at least one slit along its perimeter. Further, the second flange may be substantially circular around the majority of its perimeter, and include at least one other surface around the remainder of its perimeter. Further, the second flange may have an oblong or ovular shape. Further, the flexible body may be formed of silicone.

In another embodiment, a cannula system includes a monolithic, flexible body including a central passageway bounded by a first flange and a second flange, the first flange having a generally circular shape, the second flange having an irregular shape, and an inserter capable of gripping the second flange and altering it from a first, flat shape to a second, bent shape. Further, the central passageway may be one of generally cylindrical and generally frustoconical. Further, the second flange may include at least one slit along its perimeter, and the inserter is positioned through the central passageway and to at least one end forming the slit. Further, the cannula may have a longitudinal axis extending along the central passageway and through the first and second flanges, and wherein, with the inserter engaging at least one end forming the slit, the inserter is adapted to be rotated relative to the cannula to twist the cannula around the longitudinal axis.

In a further embodiment, a method of positioning a cannula includes engaging an inserter with the cannula, the cannula having a monolithic, flexible body including a central passageway bounded by a first flange and a second flange, the first flange having a generally circular shape and the second flange having an irregular shape, the inserter engaged with the second flange to reconfigure the second flange from a first, flat position to a second, folded position, passing at least the second flange of the cannula and the inserter into a surgical opening formed in a patient through at least one layer of tissue, moving the second flange and the inserter through the at least one layer of tissue and catching an undersurface of the layer of tissue with the second flange, releasing the inserter from the second flange, wherein the second flange returns to the first, flat position; and removing the inserter from the surgical opening.

In one embodiment, a cannula comprises a monolithic, flexible body having a central passageway bounded by a first flange and a second flange, the central passageway having an irregular shape and a diaphragm positioned therein, the first diaphragm having the same irregular shape and including at least one first diaphragm slit, and a second diaphragm positioned adjacent to or at one of the first or second flanges and having at least one second diaphragm slit. Further, at least one of the first diaphragm slits may have a shape that is non-linear. Further, the at least one first diaphragm may further comprise a plurality of slits, wherein one slit constitutes the primary slit, the primary slit having a greater length than the other plurality of slits. Further, the irregular shape may include a substantially circular portion of a first radius along a portion of a perimeter and a substantially circular portion of a second radius along the remainder of the perimeter. Further, the first diaphragm slit and the second diaphragm slit may have the same shape. Further, the first diaphragm may further comprise a diaphragm void at a radial end of the at least one first diaphragm slits. Further, the irregular central passageway may be of a cross-sectional shape including a primary portion and a secondary portion and a major dimension defined from the primary portion to the secondary portion, wherein the first diaphragm slit of the first diaphragm extends in the major dimension from a starting point within the primary portion to a radially distant end portion within the secondary portion. Further, the one of the first or second flanges may include a layer adjacent to the flange, the layer including the second diaphragm. Further, the at least one second diaphragm slit may further comprise a plurality of second slits, wherein one slit constitutes the second primary slit, the second primary slit having a greater length than the other plurality of second slits.

In another embodiment, a cannula system includes a cannula having a monolithic, flexible body having a central passageway bounded by a first flange and a second flange, the central passageway having an irregular shape extending along its length, and a first diaphragm having at least one slit, and an inserter capable of engaging at least a portion of the second flange and altering it from a first, flat shape to a second, bent shape. Further, the central passageway may further comprise a second diaphragm having the irregular shape and at least one second slit, the at least one second slit extending from the circular portion to the irregular portion. Further, the inserter may be positioned through an opening towards the second flange to engage at least a portion of the second flange. Further, the cannula may have a longitudinal axis extending along the central passageway and through the first and second flanges, and wherein, with the inserter extending through the central passageway and engaging the second flange, the inserter is adapted to be rotated relative to the cannula to twist the cannula around the longitudinal axis. Further, the irregular shape may include a substantially circular portion of a first radius along a portion of a perimeter and a substantially circular portion of a second radius along the remainder of the perimeter. Further, the at least one slit may further comprise a plurality of slits, wherein one slit constitutes the primary slit, the primary slit having a greater length than the other plurality of slits. Further, the central passageway may include a second diaphragm, the second diaphragm having a shape substantially similar to the irregular shape and including at least one second slit, the at least one slit of the first diaphragm and the at least one second slit of the second diaphragm have the same configuration. Further, the at least one second slit may have a non-linear shape. Further, the first flange may further comprise a diaphragm void at a radial end of the slit. Further, the second diaphragm may further comprise a second diaphragm void at a radial end of the second slit. Further, the first flange may further comprise a layer adjacent to the flange.

BRIEF DESCRIPTION OF THE DRAWINGS

FIGS. 6A-B are perspective views of a cannula with a separated flange according to another embodiment of the invention.

FIGS. 6C-D are bottom views of the cannula of FIGS. 6A-B.

FIG. 12A is a perspective view of a cannula with a slitted diaphragm according to another embodiment of the invention.

FIG. 12B is a bottom view of the cannula of FIG. 12A.

FIG. 12C is a cross-sectional view of the cannula of FIG. 12A.

DETAILED DESCRIPTION

Certain embodiments of the cannulas of the present disclosure are constructed of flexible material, such as silicone, to form a monolithic, flexible body. The body includes a central passageway extending between a first end and a second end for the passage of instrumentation, implants, and the like therethrough. As disclosed herein, at least one of the first and second ends may include a flange, though in most of the illustrated embodiments herein both the first and second ends include a flange.

The flange or flanges are intended to provide stability and structure to the cannula. For example, the distal flange, also referred to as the second flange, would be positioned against the interior wall of the tissue layers surrounding a surgical site to stabilize the distal end of the cannula and/or assist in expanding the surgical site by providing a proximally-directed retraction force on the interior tissue wall. Similarly, the proximal flange, also referred to as a first flange, positioned outside of the patient, may stabilize the proximal end of the flange, provide an area for the operator to grasp and manipulate the cannula, and/or provide a distally-directed compressive force against the tissue through which the cannula is positioned.

Figure 1:
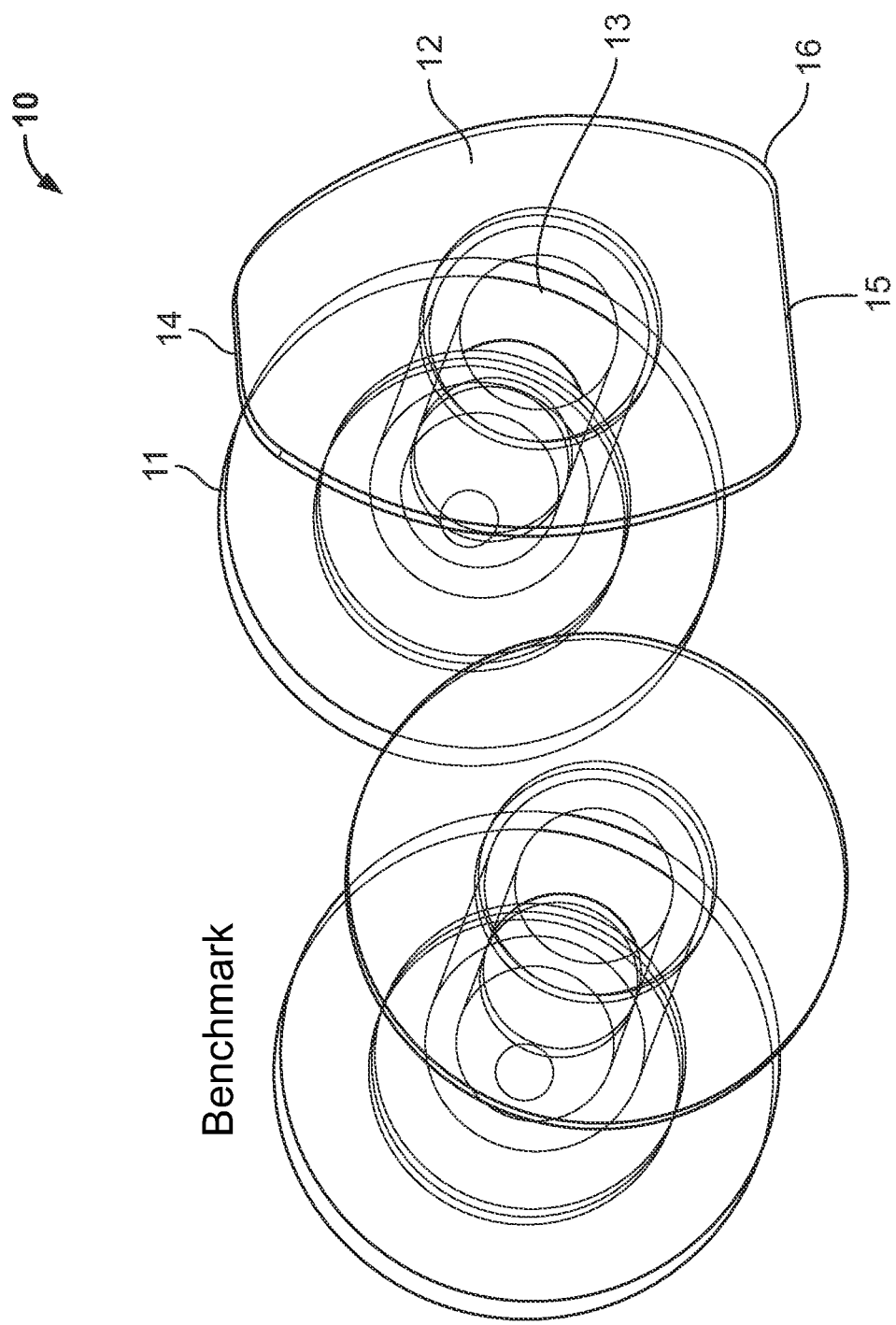
FIG. 1 is a perspective view of a cannula with an ovular flange according to one embodiment of the invention.

In one embodiment, as depicted in FIG. 1, a cannula 10 includes a first flange 11 which would be positioned outside the patient and a second flange 12 positioned against the interior tissue wall within the patient. The first flange is generally circular in shape while the second flange has an irregular shape. The body of the cannula also includes a central passageway 13 which extends between the first and second flanges to allow for passage of instruments, implants and the like therethrough. As illustrated, central passageway is generally cylindrical, though the shape may instead be frustoconical, and thus tapering either towards flange 11, towards flange 12, or towards both flanges from a narrowed middle section, or could be rectangular, ovular, or the like.

Known cannulas (illustrated in FIG. 1 as the "benchmark" cannula) have first and second flanges that are both generally circular in shape. The circular distal flange, however, upon being folded within an inserter such as a hemostat, does not provide for a structure capable of reliably "catching" the interior tissue wall. Instead, the operator is left to hope that the distal flange has progressed past the interior wall far enough into the desired surgical area (e.g., joint space) such that the distal flange will deploy and subsequently remain in the surgical area when the inserter such as a hemostat is released and removed from the distal flange. The improved shape of flange 12 of cannula 10, however, will provide a "catch" along a portion of the flange. For example, flange 12 is generally ovular or oblong in shape with a narrowed tapering portion 14 and a blunt end 15 forming corners 16. The blunt end 15 may be linear between the corners 16, as illustrated, or may have a curvature. In use, the narrowed tapering portion 14 may fold into a tapered edge suitable for leading the cannula through the tissue layers and past the interior tissue wall, while the blunt end 15, upon folding, may include corners 16 suitable for catching the interior tissue wall. In other words, once these corners 16 flex inwards to pass the interior tissue wall, they can bias back outwards from the hemostat (or other inserter) and inhibit (to some extent) removal back through the tissue layers. This biased positioning may provide sufficient tactile feedback to the operator such that she knows the second flange 12 is in the correct position and that the cannula can be disengaged from the inserter.

Further the narrow, elongated shape of second flange 12 may allow for the hemostat (or other inserter) to be positioned further away from the edges of the flange 12, thereby making the corners 16 that much more pronounced relative to the instrument and the rest of the cannula, though, the flexible construct of the cannula 10, including corners 16, may allow corners 16 to still flex and pass through the tissue layers during the insertion step.

Figure 2:
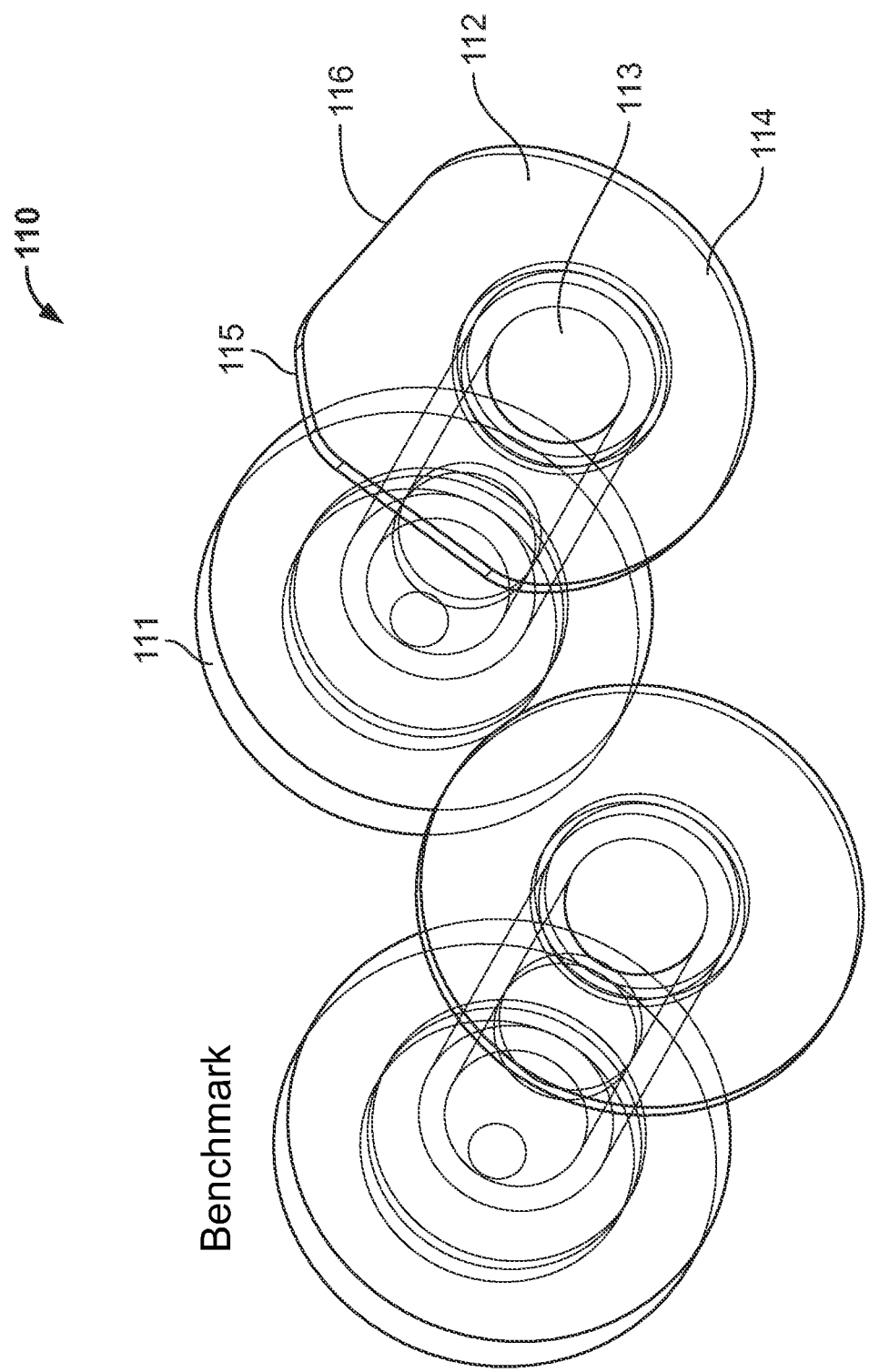
FIG. 2 is a perspective view of a cannula with an elongated flange according to another embodiment of the invention.

In another embodiment, as depicted in FIG. 2, the cannula 110 includes a first flange 111 which would be positioned outside the patient and a second flange 112 positioned against the interior tissue wall within the patient. The first flange is generally circular in shape while the second flange has an irregular shape. The body of the cannula also includes a central passageway 113 which extends between the first and second flanges to allow for passage of instruments, implants and the like therethrough. As illustrated, the central passageway is generally cylindrical, though the shape may instead be frustoconical, and thus tapering either towards flange 111, towards flange 112, or towards both flanges from a narrowed middle section, or could be rectangular, ovular, or the like.

As with the previous embodiment in FIG. 1, an example of a known cannula is included for the sake of comparison. Cannula 110 includes distal flange 112 that has an irregular shape, which as illustrated includes a generally circular portion 114 around a substantial portion, or majority, of the perimeter of flange 112, and includes at least one surface 116 around the remainder of its perimeter, and as illustrated, includes two flat surfaces 116 positioned on either side of an elongated tip 115. The flat surfaces 116 may instead have a curvature instead of being linear as illustrated.

Figure 3:
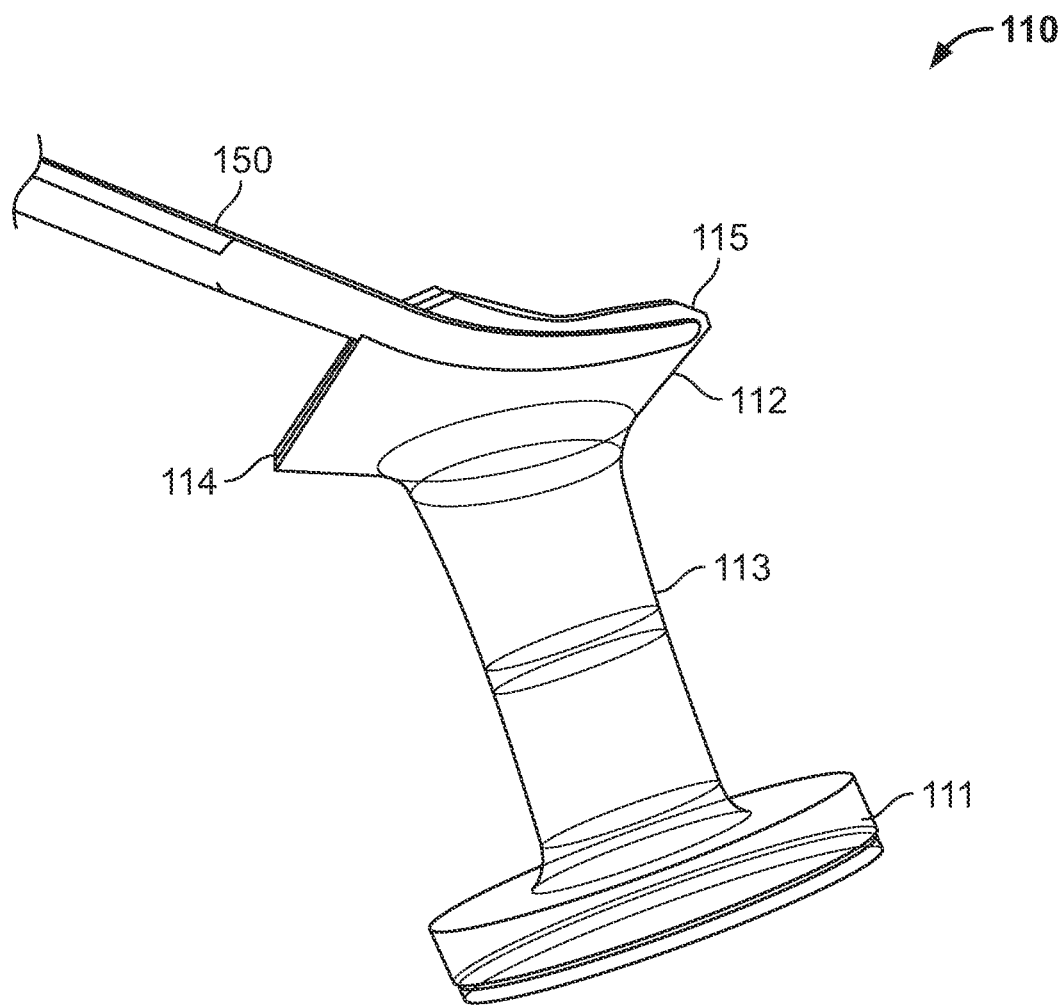
FIG. 3 is a side view of a cannula with a low-profile flange according to a further embodiment of the invention.

Continuing with this embodiment of FIG. 2, the shape of flange 112 also allows for an inserter-cannula configuration that differs from those disclosed above. As illustrated in FIG. 3, the inserter, or hemostat 150, has been positioned to generally coincide with the lower profile of the leading end of flange 112, including surfaces 116 and elongated tip 115. Further, the leading edge of the flange, having a relatively longer shape, may allow the hemostat to engage that portion, leaving the circular perimeter exposed and extending away from the hemostat. Keeping the perimeter 114 exposed, and keeping the hemostat positioned on the leading end, may provide for a pronounced barb surface (as annotated below), formed by the circular perimeter 114, which again due to the materials of construction (e.g., silicone) and/or the shorter width of circular perimeter 114, will still be capable of flexing to pass through the tissue layers during the insertion step.

Figure 4:
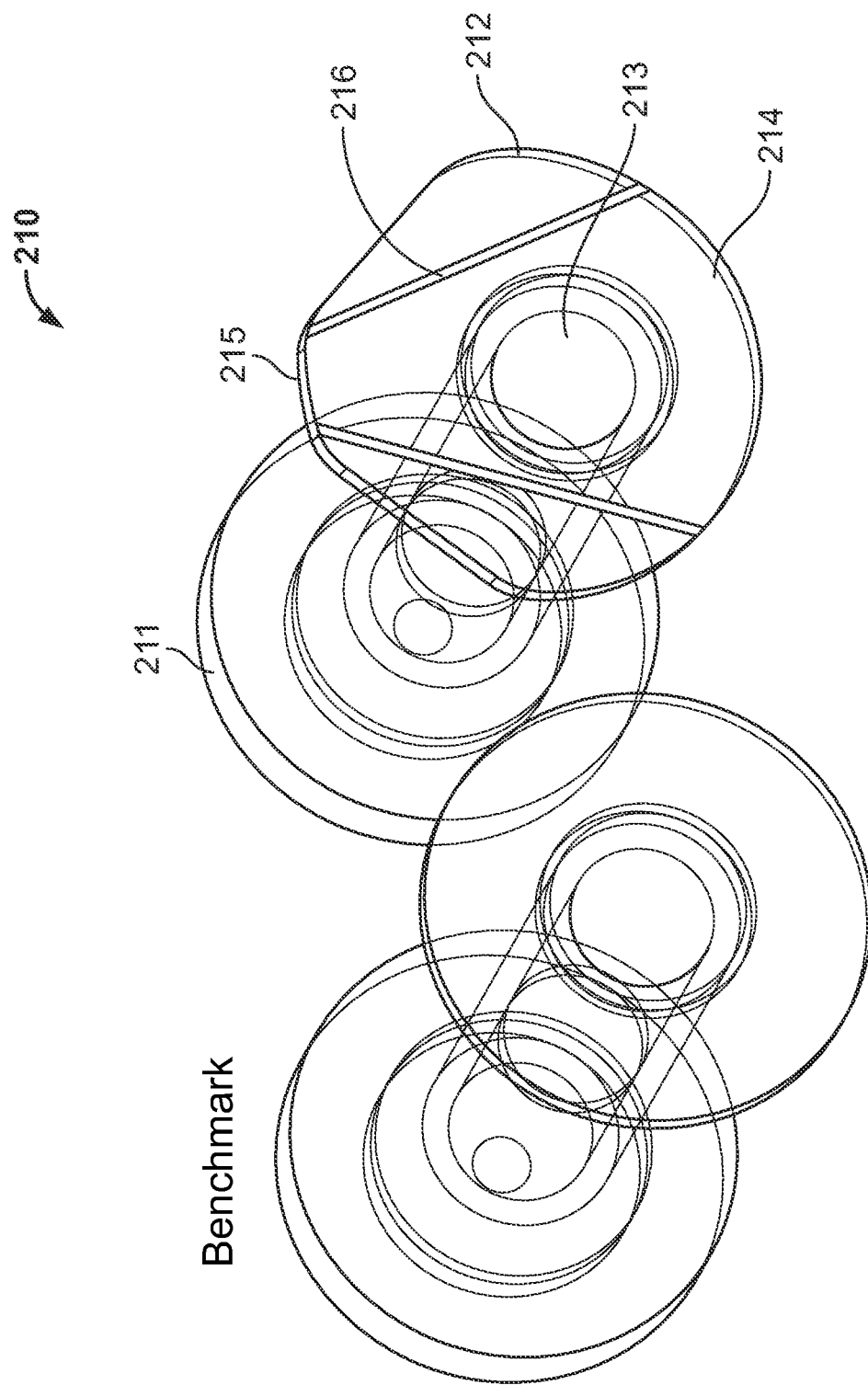
FIG. 4 is a perspective view of a cannula with an elongated flange according to yet another embodiment of the invention.
Figure 5:
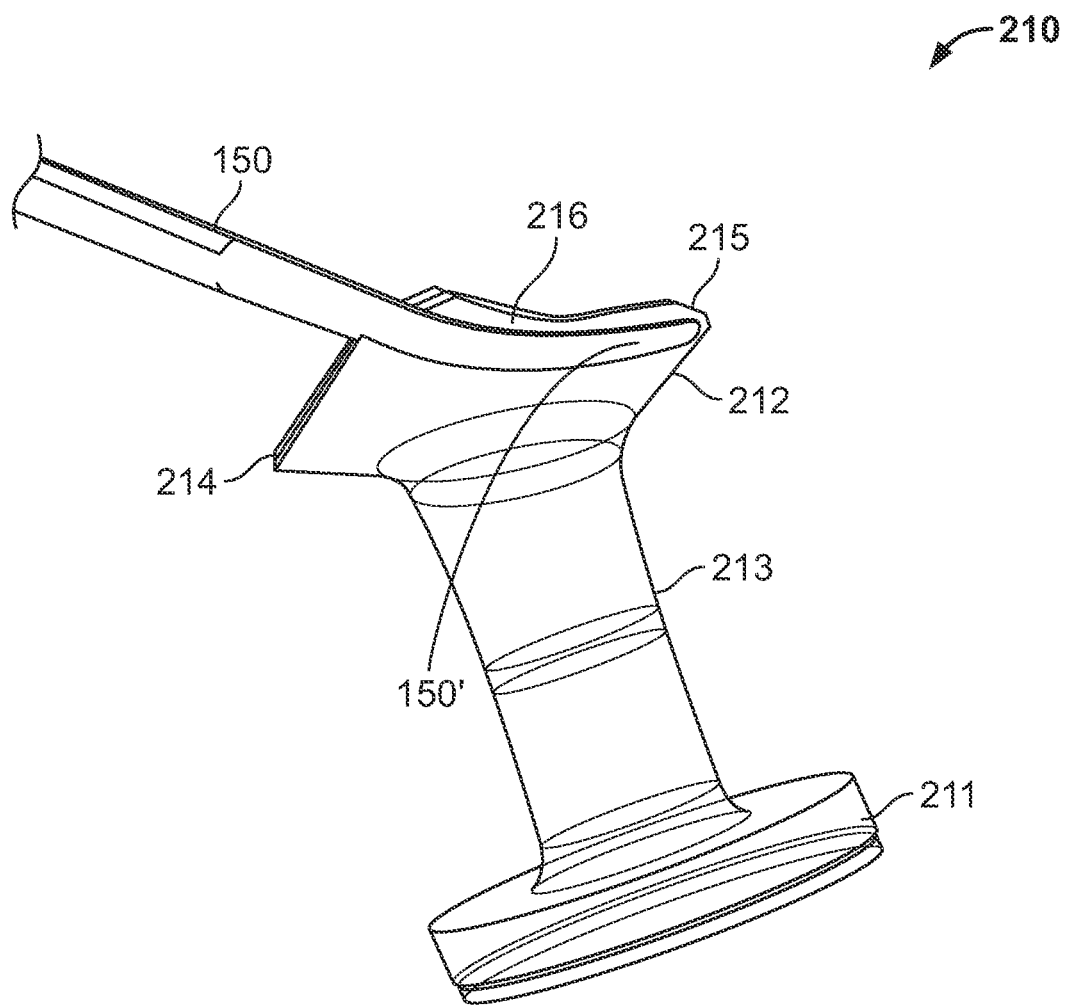
FIG. 5 is a side view of a cannula with a low-profile flange according to still another embodiment of the invention.

In yet another embodiment, as depicted in FIG. 4, the previous embodiment of cannula 110 is further modified as cannula 210 to include an alternative low-profile distal flange and, as exemplified in FIG. 5, may provide for a new positioning of the hemostat which may allow for further simplification of insertion of the cannula into the patient. As illustrated in FIGS. 4-5, cannula 210 is similar to cannula 110 above, and thus like reference numbers denote like reference numbers. In this embodiment, surfaces 216 have been elongated (denoted by white lines in FIG. 4 and red line in FIG. 5) such that a larger amount of flange 212 has been removed.

A greater amount of flange 212 may be removed in light of the positioning of the hemostat 150 relative to cannula 210. As illustrated in FIG. 5, the hemostat 150 is flipped relative to the previous embodiment, to a new position of hemostat 150', and positioned more proximally such that its jaws engage the leading end of flange 212, along surfaces 216 and elongated tip 215, as well as along at least a portion of central passageway 213. As with the prior embodiment, this positioning of hemostat 150' may provide for a pronounced barb surface formed by the circular perimeter 214, which again may be due to the materials of construction (e.g., silicone) and/or the shorter width of circular perimeter 214, which may still be capable of flexing and passing through the tissue layers during the insertion step.

In still another embodiment, as depicted in FIGS. 6A-D, cannula 310 includes a first, proximal flange 311 and a central passageway 313, as in the various embodiments above, as well as a second, distal flange 312. In this embodiment distal flange 312 includes a separation 320 along its perimeter, formed by a first end 321 and a second end 322, which may or may not overlap one another. As illustrated in FIGS. 6A-D, separation 320 and ends 321, 322 can overlap as much as desired, or not overlap at all, though, to help ensure a watertight seal at flange 312, there should be at least some overlap to seal the area where the separation is present. Further, the sketches below illustrate that flange 312 can be of any shape desired, whether generally circular, ovular or oblong, irregular (e.g., such as any of the flanges 12, 112, 212 described above), or the like.

Figure 7A:
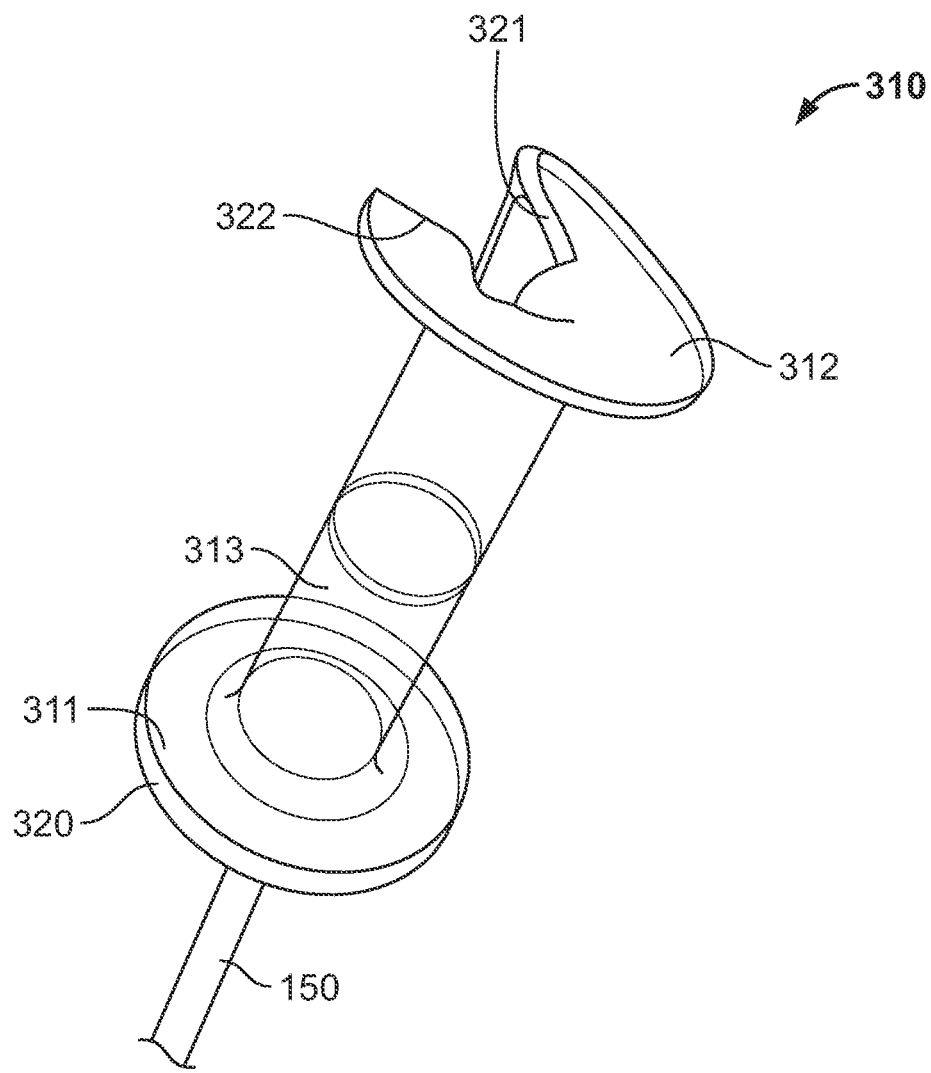
FIG. 7A is a perspective view of a cannula with a separated flange along with an inserter, such as a hemostat as illustrated, according to a further embodiment of use of the invention.
Figure 7C:
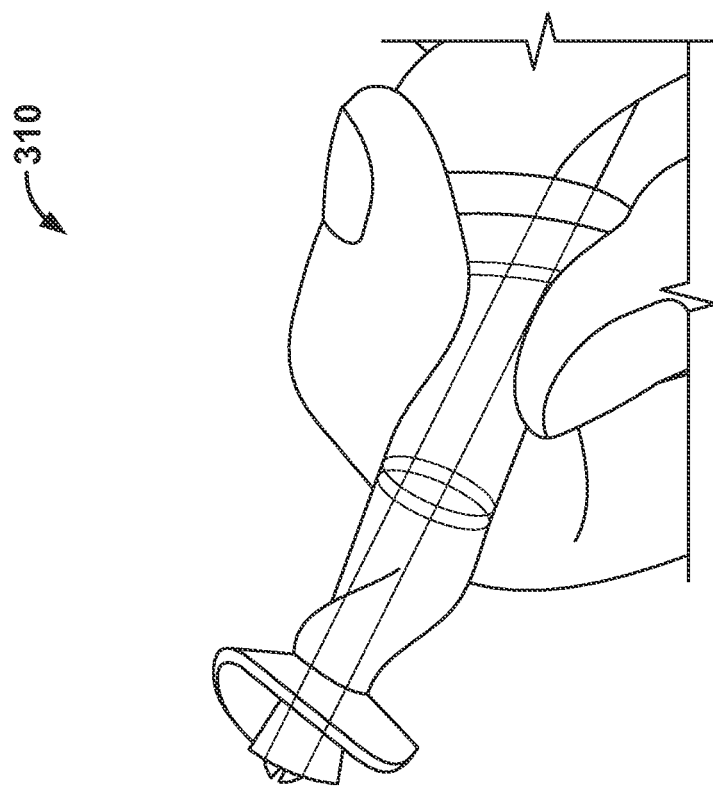
FIGS. 7B-C are perspective views of the cannula of FIG. 7A along with an inserter, such as a hemostat as illustrated, shown in another configuration.
Figure 7B:
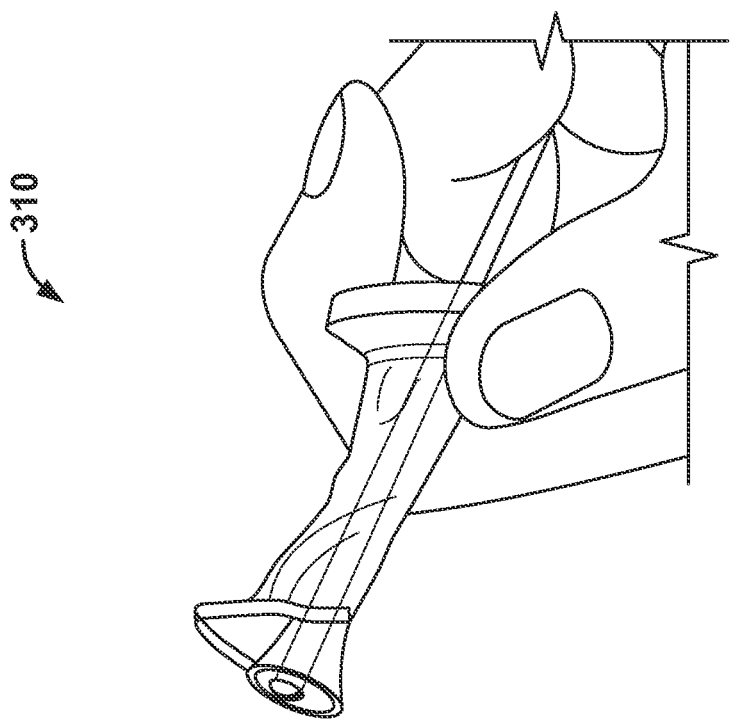

The separation 320 may provide an advantage during insertion of the cannula 310 into the patient. One exemplary embodiment of a method of insertion will now be described and is illustrated in FIGS. 7A-C. The method of this embodiment includes the first step of positioning an inserter, such as hemostat 150, through the central passageway 313 of cannula 310 from a proximal end (flange 311) to a distal end (flange 312). At the distal end, the hemostat 150 grasps or otherwise engages one end 321 or 322 at separation 320.

With the hemostat 150 so positioned, the proximal flange 311 may be held stationary while hemostat 150 is rotated relative to flange 311, such that the cannula 310 body starts twisting around itself, such that is establishes a twisted shape, similar to a "waffle cone" shape. Such a twisted shape should result in a narrowing or tapering of the distal end of the cannula 310, including at flange 312 in particular as end 321 is continuously tucked further and further underneath the rest of flange 312 as the cannula is twisted.

Cannula 310 in this position is ready for insertion into a patient. As such, the flange 311 is held relative to hemostat 150 and the tapered distal end, including flange 312, is inserted through the surgical opening, through the tissue layers and past the interior tissue wall. As discussed above, and as illustrated in FIGS. 7B and 7C, the distal flange 312 in this twisted configuration provides a projection or barb that may give the operator tactile feedback that the flange 312 has passed the interior tissue wall and is ready for release and final positioning.

Cannula 310 may be released by disengaging hemostat 150 from the flange 312, such that cannula 310 returns to its original, untwisted position. Alternatively, it is also possible to rotate hemostat 150 in the opposite direction relative to flange 311 to unwind cannula 310, at which point hemostat 150 may be detached from end 321 (or end 322, as desired). Cannula 310 may at this point be further adjusted by the operator as desired to obtain proper interior tissue wall compression (to expand joint space), orientation of central passageway 313, or the like.

Similarly, removal of the cannula 310 may be performed by conducting the above steps in reverse. While flexible cannulas of the prior art is simply pulled out manually, or by using a hemostat to grab and constrict the cannula, cannula 310 may also be removed by again positioning hemostat 150 within the central passageway 313, engaging one of the ends 321, 322, and, while holding flange 311 stationary, rotating hemostat 150 to twist the cannula into a twisted, tapered shape. Such a method of removal may simplify removal and minimize any risks of damage to the tissue layers, tearing of the cannula, or the like.

Figure 8:
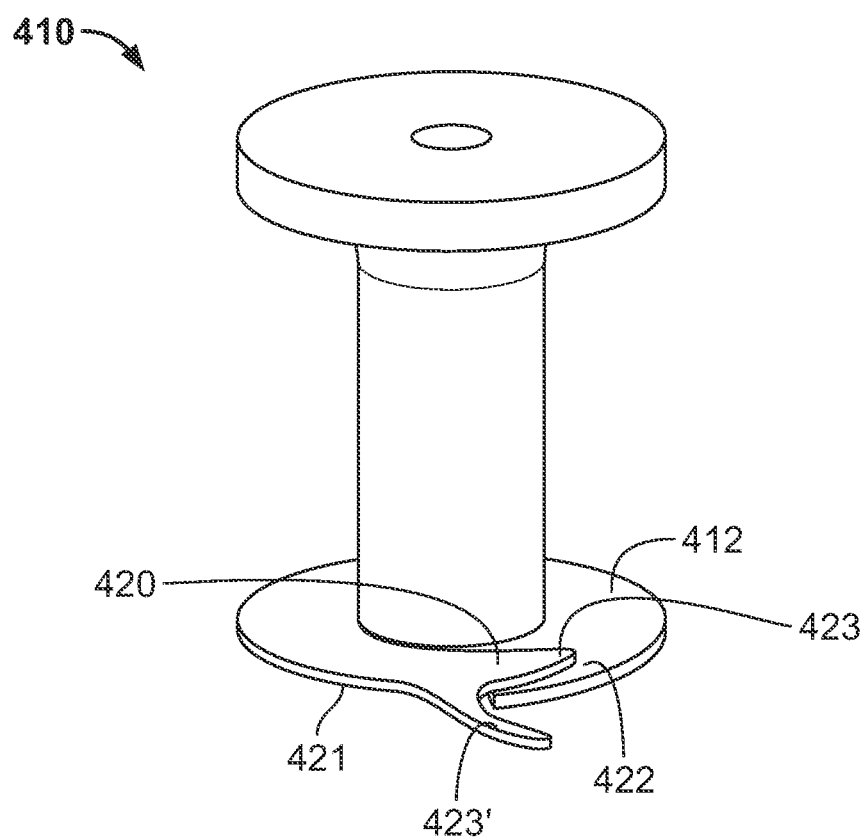
FIG. 8 is a perspective view of a cannula with a separated flange according to another embodiment of the invention.

As depicted in FIG. 8, a further embodiment of a cannula 410 may include a separation 420, similar to that discussed above. Further in this embodiment, at least one of the formed ends 421, 422 may include first and second flaps 423, 423'. As in the annotations below, the top flap 423 may serve to further seal the distal flange 412 at the separation 420, while the bottom flap 423' may provide a portion of the end 421, 422 that can be engaged by the hemostat 150 (or other inserter).

Figure 9:
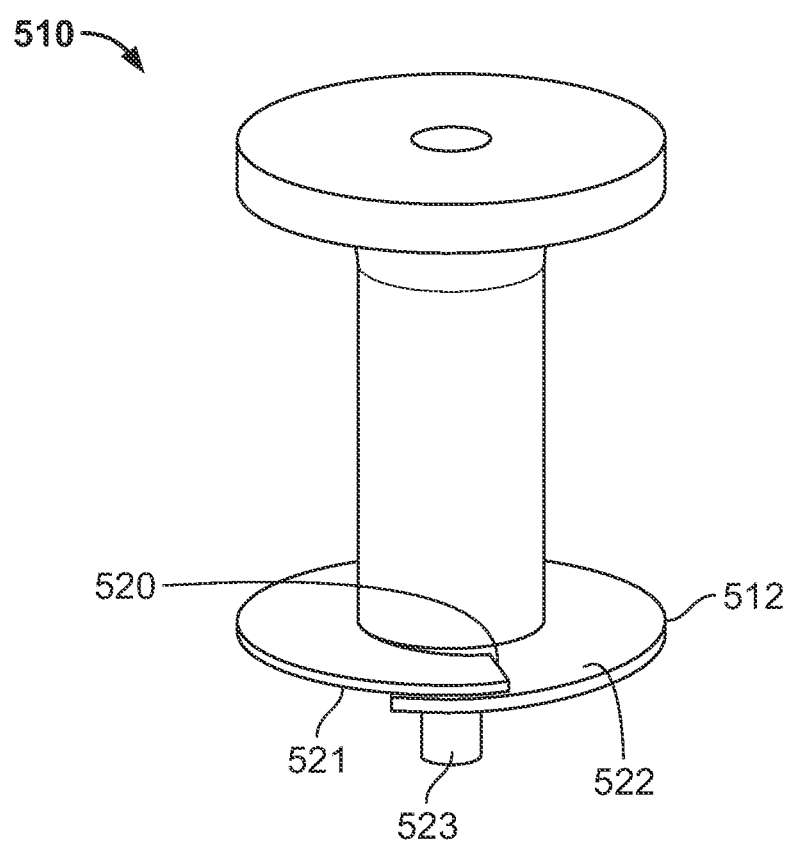
FIG. 9 is a perspective view of a cannula with a separated flange according to yet another embodiment of the invention.

In yet another embodiment, as depicted in FIG. 9, flange 512 of cannula 510 may again include separation 520 and formed ends 521, 522. In this embodiment, at least one of ends 521, 522 may include a tab 523 which may improve the ability to grasp the end 521 or 522, and further, may provide a more stable engagement of the inserter to the grasped end 521 or 522.

Figure 10:
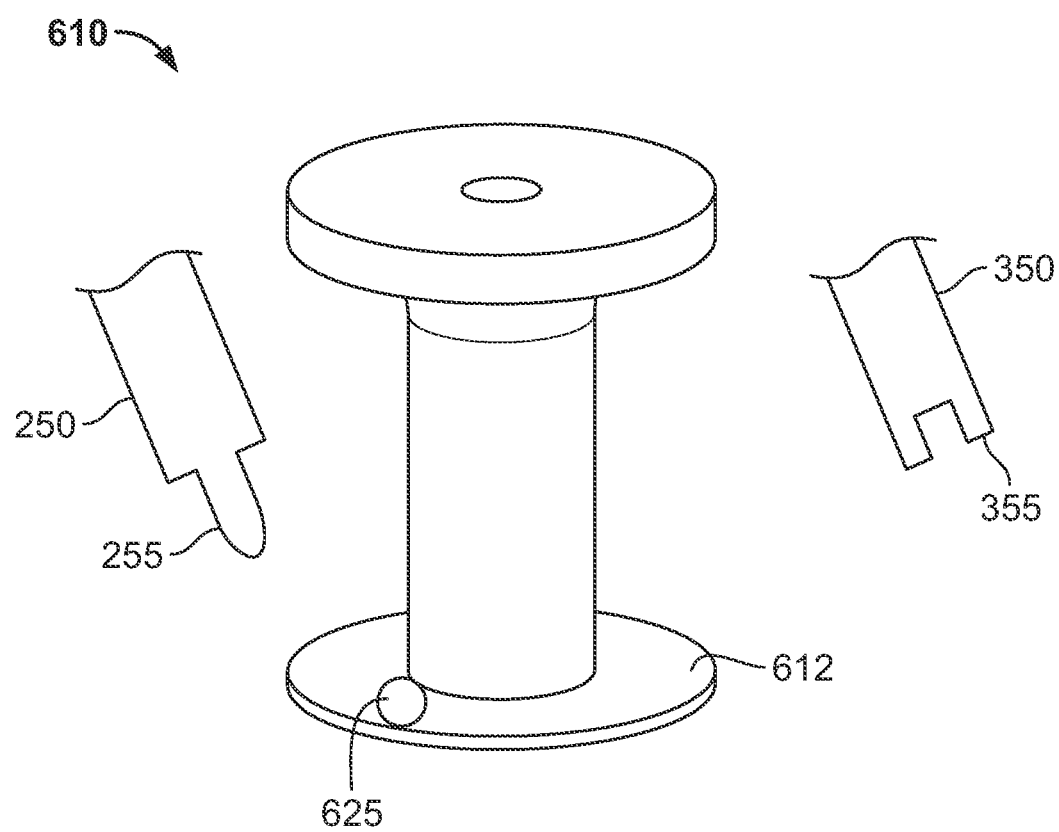
FIG. 10 is a perspective view of a cannula with a holed flange according to yet a further embodiment of the invention.

In another embodiment, as depicted in FIG. 10, a system can include an inserter and a cannula. While, as above, a hemostat or like inserter may be used, in this embodiment, an inserter including a distal engagement feature may engage a hole or other engagement feature on the cannula. As illustrated, for example, an inserter 250 or 350 of this embodiment can either have a stepped distal tip 255 or a forked distal tip 355, either of which can engage an at least one hole 625 positioned on one or both flanges of the cannula 610. As illustrated, the hole 625 can be positioned on distal flange 612.

In use, the inserter tip 255, 355 can be positioned in hole 625. The cannula may then be forced through the surgical opening in the patient. Alternatively, the cannula can be folded or otherwise wrapped around inserter 250, 350 before inserting into the surgical opening, as discussed above, to provide a more tapered shape for ease of insertion.

Figure 11C:
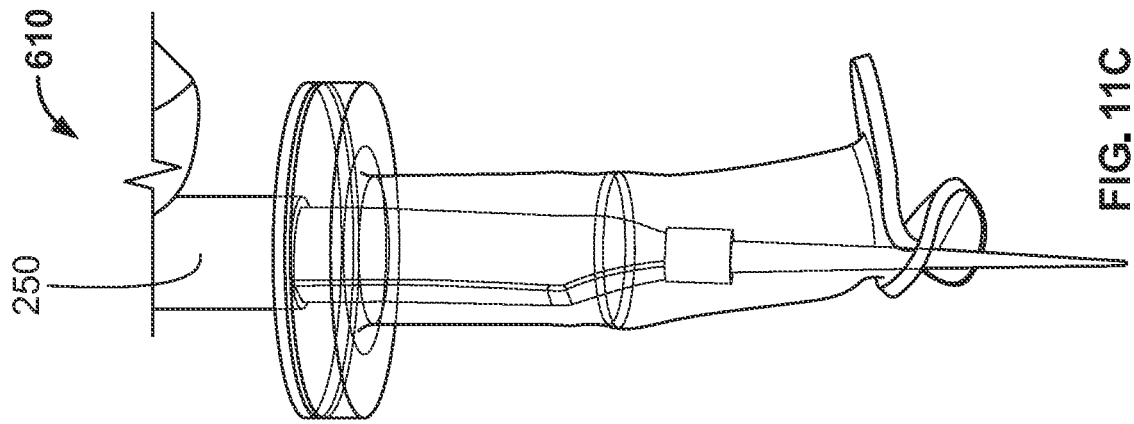
FIG. 11A-C are a perspective view of the cannula of FIG. 10 in one embodiment of use of the invention.
Figure 11B:
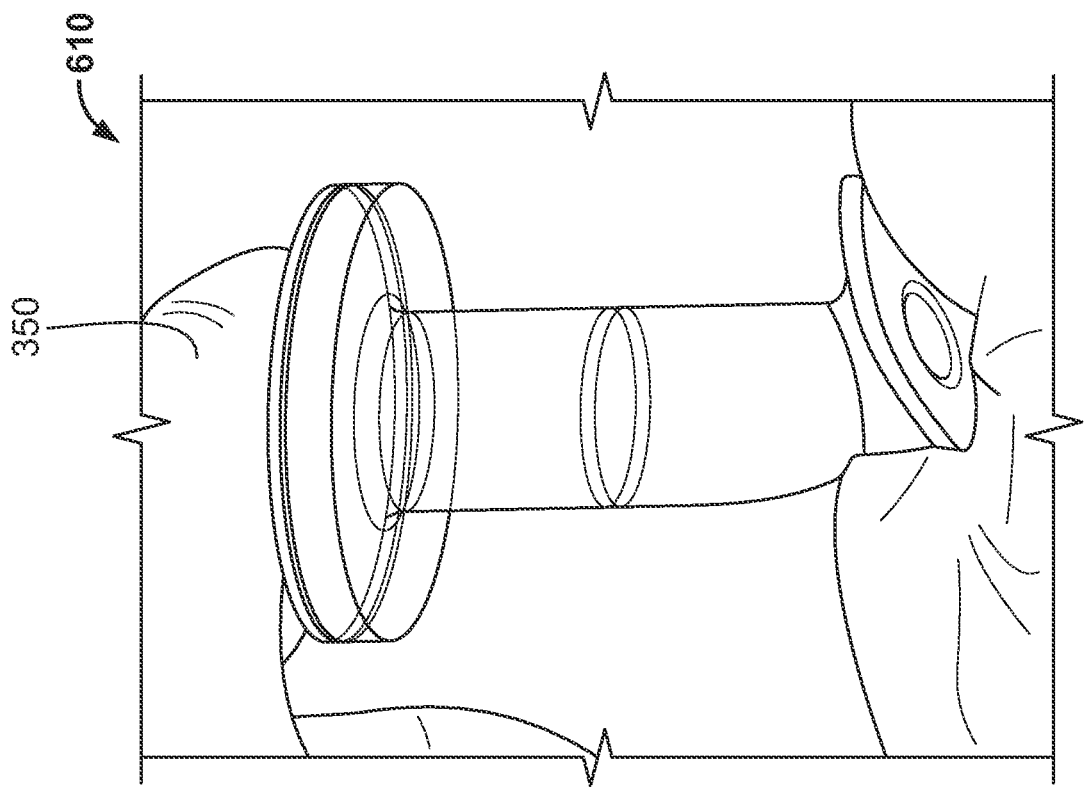
Figure 11A:
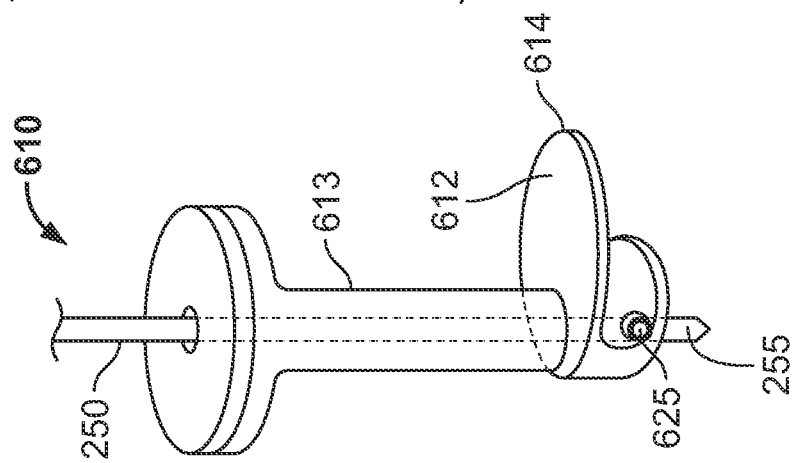

Another method of inserting a cannula of the present disclosure is illustrated in FIGS. 11A-C. In this embodiment, cannula 610 and inserter 250 are used similar to cannula 310 and hemostat 150, in that inserter 250 is positioned through central passageway 613 of cannula 610. In this configuration, the inserter may be positioned through the central passageway 613. The operator may then fold flange 612 over to align hole 625 with distal tip 255 such that distal tip is passed through hole 625 and to a position distal to the cannula 610. In this configuration, the distal flange 612, as in the various embodiments above, takes on a tapered shape while providing a projection or barb 614 to provide tactile feedback to the operator upon passing the interior tissue wall.

Although FIG. 10 depicts cannula 610 as having one hole 625, it is envisioned that, in other embodiments, there may be any number of holes on the distal flange. By way of example, there may be two holes on either side of the central passage way. In such a configuration, both portions of the distal flange are folded towards each other such that their respective holes align with the distal tip 255 of the inserter such that the tip can be passed through both holes. In this manner, an even smaller distal profile may be provided prior to insertion within the tissue.

In another embodiment, there are a plurality of holes on the distal flange, but none of them align with each other upon flexing the distal flange. However, in such a configuration, the distal tip of the inserter may comprise multiple projection(s) to engage both holes, such as forked tip 355. As described above, distal flange 612 may be circular or non-circular. In one embodiment, it is non-circular (e.g. oblong) with the holes residing in the extended portion of the flange.

Any of the various features in the above-discussed embodiments may be utilized on a cannula in any configuration or combination desired. For instance, a separation may be included on an irregularly-shaped flange, and one end formed by the separation may include a tab and/or multiple flaps as desired. Alternatively, an inserter, including any of inserters 150, 250, 350 may be utilized with any cannula as desired. Similarly, it is envisioned other design features may be included in any of the above-described cannulas. For example, the central passageway may be generally cylindrical, ovular, rectangular, frustoconical, and thus tapering either proximally towards a proximal flange (if present), distally towards a distal flange (if present), or towards both proximal and distal directions from a narrowed middle section, or the like, or any combination thereof. Also, the cannula may have a diaphragm positioned within the central passageway to inhibit leakage of surgical and body fluids, as is known in the art. Typically, such a diaphragm is a tri-cuspid design and allows the passage of instruments therethrough but otherwise works to prevent leakage of fluid back out of the patient. The diaphragm may be positioned at any location in the central passageway, whether adjacent the distal or proximal end, or somewhere in between the distal and proximal ends. Further, more than one diaphragm may be included, if desired.

In another embodiment, as depicted in FIGS. 12A-C, cannula 710 has central passageway 713, proximal flange 711, and distal flange 712, as described above. In this embodiment, proximal flange 711 has an irregular shape having a generally circular primary portion 721 and a generally circular secondary portion 722 (see FIG. 12C), with distal flange 712 having a substantially similar shape. The generally circular shapes of the primary and secondary portions may be formed of arcs with different radii, though they may alternatively be formed of arcs with the same radii. These primary and secondary portions collectively form a central passage 713 which similarly includes a primary portion 721' and a secondary portion 722'. Further, using this embodiment as an example, the resulting shape of the central passageway 713 has a length extending from the primary portion 721' into the secondary portion 722', and a width extending perpendicular to the length, whereby the length is longer than the width. As used herein, such a length will be considered the major dimension of the passageway 713.

On the proximal face of proximal flange 711 lies a layer 724 which may have the same shape as proximal flange 711. Layer 724 includes a first diaphragm 725 including an opening 720, slit 715 and optionally, a radially-spaced void 714. Opening 720 allows for instruments (e.g. a hemostat, grasper, suture retriever, suture passer, suture anchor and insertion instrument, drill, or the like) and/or sutures to be inserted within central passageway 713. Cannula 710 may further include a second diaphragm 716, or diaphragm 716 may alternatively serve as an alternative diaphragm to layer 724. As illustrated in FIG. 12B, second diaphragm 716 may include a second diaphragm slit 718 and optionally, a radially-spaced void 719, which may be positioned at the same radial orientation as slit 715 and void 714 of first diaphragm 725, if present. Diaphragm slits 715, 718 and voids 714, 719 may be sized to maintain at least one suture within the void/slit area, such that it may separate such one or more sutures radially spaced from the primary portion 721'. Similarly the center of opening 720 lies along the same longitudinal axis as center 723 of diaphragm 716. Further, center 723 may be defined by the intersection of slit 718 and secondary slits 717. Secondary slits 717 and second diaphragm slit 718 extend in radial directions away from center 723. As illustrated, slits 717, 718 may be radially spaced at substantially equal angles from one another to form a traditional tricuspid design, though other angles are envisioned. In this manner, slit 718 may serve two functions: one as part of the tri-cuspid seal; and the other for retaining one or more sutures. As illustrated, secondary slits 717 may be positioned primarily or entirely within primary portion 721' while second diaphragm slit 718 extends radially from primary portion 721' and, as illustrated, can extend into at least part of secondary portion 722'. As discussed, the longer dimension of slit 718 relative to slits 717 extends along the major dimension of passageway 713 such that a suture positioned within slit 718 and void 719 (if present) is spaced radially away from center 723 and primary portion 721', and parked within the secondary portion 722' such that the primary portion 721' of passageway 713 can be used for the passage of instruments, other sutures, or the like while minimizing interference with the "parked" suture. In the alternative, if desired, slits 717 may also be capable of parking a suture or sutures therein. In this fashion, it is envisioned that, for example, one suture can be parked within slits 715 and 718, and thus in the secondary portion 722' of passageway 713, while another suture is parked within one of slits 717.

Layer 724 may be fused, adhered, or securely engaged with the proximal face of proximal flange 711 by means known by one skilled in the art. Alternatively, layer 724 may be an integral part of cannula 710, or further, a first diaphragm 725 may instead be integrated into proximal flange 711 such that layer 724 is not included. In yet another embodiment, the layer 724 is not included and the first diaphragm is positioned adjacent to the proximal flange and within the proximal end of the central passageway. In such an embodiment, the diaphragm 725 may be positioned within the cross-section of the proximal flange 711 or just distal to the proximal flange 711.

Although FIGS. 12A-B depicts second diaphragm slit 718 as being longer than secondary slits 717, it is envisioned that, in other embodiments, each of the diaphragm slits may have any length with respect to each other. The first diaphragm and second diaphragm may each have one or more slits, though as illustrated in this embodiment the first diaphragm has only one slit and the second diaphragm has three slits total. In other embodiments, the first and second diaphragms (or a single diaphragm, or more than two diaphragms) may each be of any shape (e.g. substantially circular, the same shape as the central passageway, or the like), have any number of slits, and such slits may be of any length. While the intention of slits 715, 718 is to provide a pathway for a suture to move radially away from the primary portion 721' and into the secondary portion 722, the starting point of the slit (e.g., center 723) may be positioned anywhere within the area of the primary portion 721', or even partially into the area of the secondary portion 722', while the secondary slits 717 may extend within the primary portion 721' and towards and/or into the secondary portion 722'. These varying shapes may still allow for positioning at least one suture radially away from the primary portion 721' and into the secondary portion 722', while providing access for other sutures, instruments, or the like in the primary portion 721'.

Layer 724 (or diaphragm 725 if no layer is present) and diaphragm 716 may be made of the same flexible material as the rest of cannula 710 such that the material surrounding slits 715, 717, and 718 can be maneuvered to allow at least one suture to pass therethrough and be held in place. The thickness of the two diaphragms can be adjusted as desired to impart greater or less flexibility and thus friction on the suture parked therein.

Figure 18:
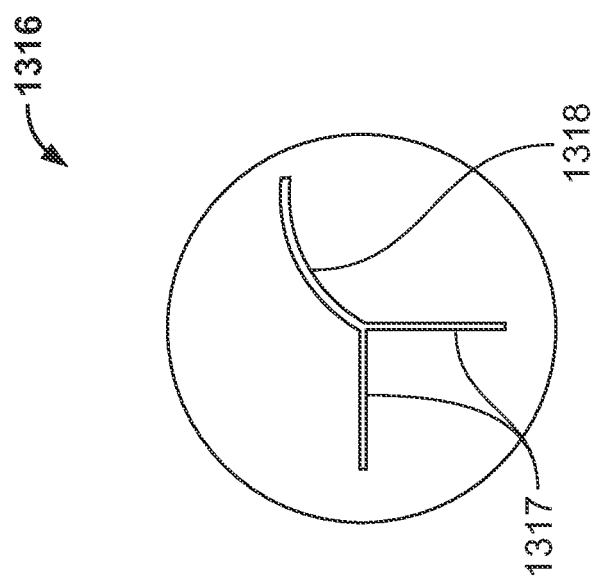
FIG. 18 is a cross-sectional view of a cannula with a diaphragm with a clockwise slit having no void according to still another embodiment of the invention.
Figure 17:
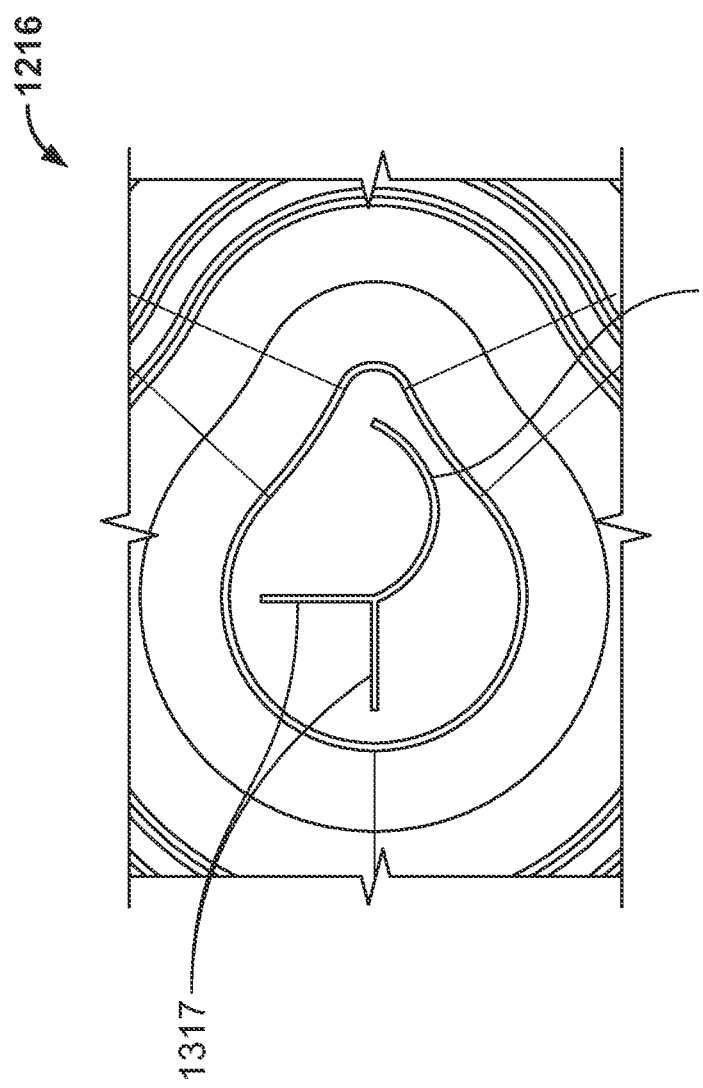
FIG. 17 is a cross-sectional view of a cannula with a diaphragm with a counter-clockwise slit having no void according to another embodiment of the invention.

FIG. 12C depicts a cross-sectional view of central passageway 713 having a primary portion 721 and secondary portion 722 forming a "tear drop" shape along the length of central passageway 713. Central passageway 713 may have any shape desired, other examples of which are illustrated herein (e.g. a substantially circular portion of a first radius along a portion of a perimeter and a substantially circular portion of a second radius along the remainder of the perimeter, portions having perimeters of other shapes than circular, or any combination of shapes, or the like). In this example, cannula 710 includes a proximal flange, a distal flange, and a central body all of which have a generally tear drop shape. Further, slits 715, 718 and voids 714, 719 are positioned along the same longitudinal axis so as to align with secondary portion 722 such that the one or more sutures positioned therein can be positioned through the secondary portion and the two voids and/or slits. In such a configuration, the suture can be positioned radially away from the primary portion 721 of passageway 713, thereby minimizing interaction between the one or more sutures and any instruments, or other sutures, positioned in the primary portion 721. In alternative embodiments, at least one of first diaphragm 725 and second diaphragm 716 may have no voids 714, 719. In such a configuration, the suture can be positioned along the length, or at the radially distal portion of, any of slits 715, 717, 718. In further embodiments, FIGS. 17 and 18 depict cross-sectional views of exemplary diaphragms 1216, 1316 having secondary diaphragm slits 1217, 1317 and diaphragm slits 1218, 1318, similar to those described above. In this embodiment, there are no voids at the radial end of slits 1218, 1318.

Although FIGS. 12A-C depict proximal flange 711 and distal flange 712 as having a similar shape, it is envisioned that, in other embodiments, the proximal and distal flanges may have separate shapes (e.g. the distal flange has an irregular shape while the proximal flange is circular). In another embodiment, the diaphragm(s) may have any number of slits (e.g. three slits). In yet another embodiment, the diaphragm(s) may have any number of voids (e.g. none, or one void at the radial end of at least one slit, or all of the slits). In yet another embodiment, the secondary portion of the passageway may extend along only a portion of the length of the passageway. In most embodiments, while the flanges may be of any shape, it would be preferable for a slit and optionally a void of the one or more diaphragms to be aligned with the secondary portion such that the one or more sutures can be positioned and parked within both the void/slit structure(s) and the secondary portion, and thus, be spaced apart from the primary portion of the passageway.

Figure 13:
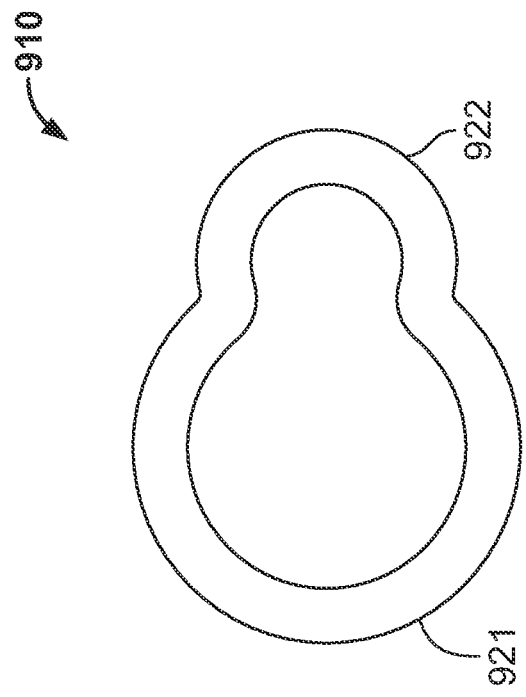
FIG. 13 is a cross-sectional view of a cannula with an irregular shape according to yet another embodiment of the invention.
Figure 14:
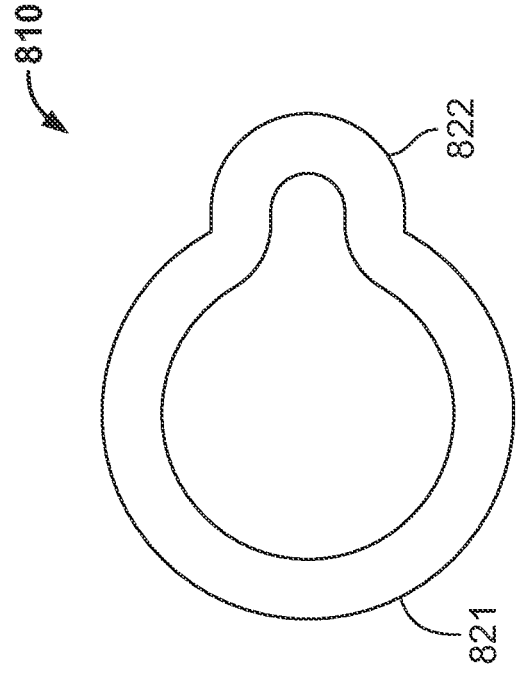
FIG. 14 is a cross-sectional view of a cannula with an irregular shape according to a further embodiment of the invention.

In other embodiments, FIGS. 13 and 14 depict cross-sectional views of cannulas 810, 910 having a primary portion 821, 921, as described above. In these embodiments, secondary portions 822, 922 are illustrated as having varying sizes. Although FIGS. 13 and 14 depict secondary portions 822, 922 as being of a smaller size than primary portions 821, 921, it is envisioned that, in other embodiments, the secondary portion may be of an equal size to the primary portion. In another embodiment, the secondary portion may be rectangular, triangular, or any other shape known by one skilled in the art. In yet another embodiment, there may be no distinct secondary portion, and the cross-sectional shape of the central passageway may instead be that of an ellipsis, rectangle, triangle, or any other shape known by one skilled in the art. In yet another embodiment, there may be any number of secondary portions extending from the primary portion (e.g. three secondary portions extending from a primary portion similar to a three-leafed clover, or other shapes such as a diamond, star-shape, or the like). Using the shape of an ellipsis as an example, a diaphragm used with such a passageway may include at least one slit extending along the major dimension of the ellipse to, as discussed above, provide a radial path to move and park a suture away from the primary portion of the central passageway (e.g. defined by the minor axis of the ellipse) where other sutures, instruments, and the like may be passed.

Figure 16:
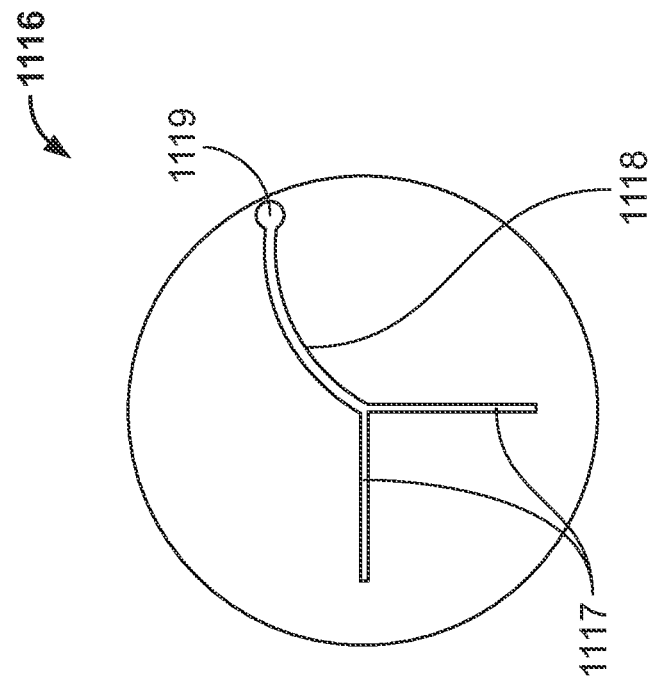
FIG. 16 is a cross-sectional view of a cannula with a diaphragm with a clockwise slit according to still another embodiment of the invention.
Figure 15:
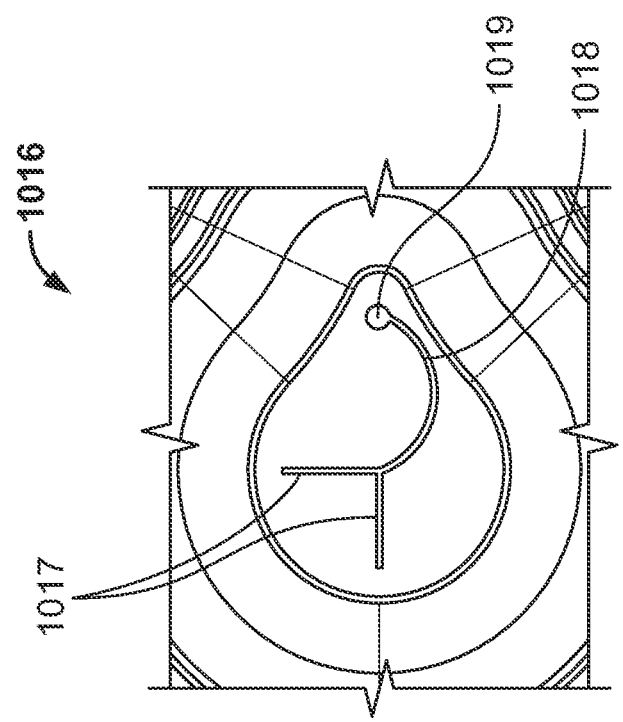
FIG. 15 is a cross-sectional view of a cannula with a diaphragm with a counter-clockwise slit according to another embodiment of the invention.

In still further embodiments, FIGS. 15 and 16 depict cross-sectional views of exemplary diaphragm 1016, 1116 having secondary diaphragm slits 1017, 1117 and diaphragm slits 1018, 1118 extending to optional voids 1019, 1119, similar to those described above. In these embodiments, slits 1018, 1118 are non-linear such that they are curved. Slit 1018 is curved in a counter-clockwise direction. Second diaphragm slit 1118 is curved in a clockwise direction. Although FIGS. 15 and 16 depict slits 1018, 1118 as being curved, it is envisioned, in other embodiments, that such slits may have other generally non-linear shapes such as including angles, "L" shapes, zig-zags, or any other shape known to one skilled in the art. In another embodiment, secondary slits 1017, 1117, if present, may also be generally non-linear, such as curved, angled, zig-zagged, or any other shape known to one skilled in the art. Such various non-linear shapes may be useful in providing additional friction to maintain the one or more sutures within the slit/void construct while the user performs other surgical activity through the main passageway.

While the first and second diaphragms of the embodiments of FIGS. 12-17 are illustrated as being located at the proximal flange and within the passageway, respectively, such a cannula may have one or more diaphragms, and the one or more diaphragms may be positioned anywhere along the length of the cannula. In other embodiments, it is envisioned that an inserter, such as a hemostat, as described above, may be used with the cannulas as shown in FIGS. 12-17 to insert the cannula through the tissue.

In yet another embodiment, a method of using a cannula of any of FIGS. 12-17 includes positioning such a cannula in a patient. Positioning the cannula may be performed by hand or with the use of an inserter, such as a hemostat. A surgical procedure may be initiated by the user such that, at some point, at least one suture is positioned through the passageway of the cannula. Once the at least one suture has been manipulated as desired, the user may park the suture by moving the suture radially to pass into a first slit on each of one or more diaphragms of the cannula. The first slit(s) maintain the suture in the radial position in the secondary position. The user may then utilize the primary portion of the central passageway of the cannula to perform other surgical procedures, such as by passing an instrument or additional sutures therethrough. The user may at any time grasp the suture positioned in the slit(s) and move the suture back radially inwards towards the center of the cannula and out of the slit(s).

Figure 19B:
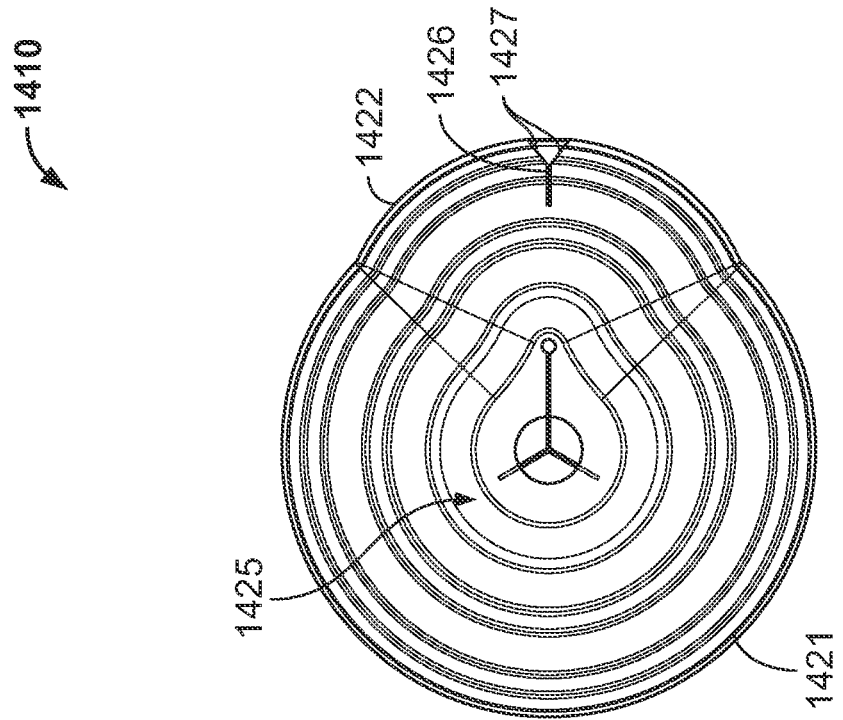
FIG. 19B is a top view of the cannula of FIG. 19A.
Figure 19A:
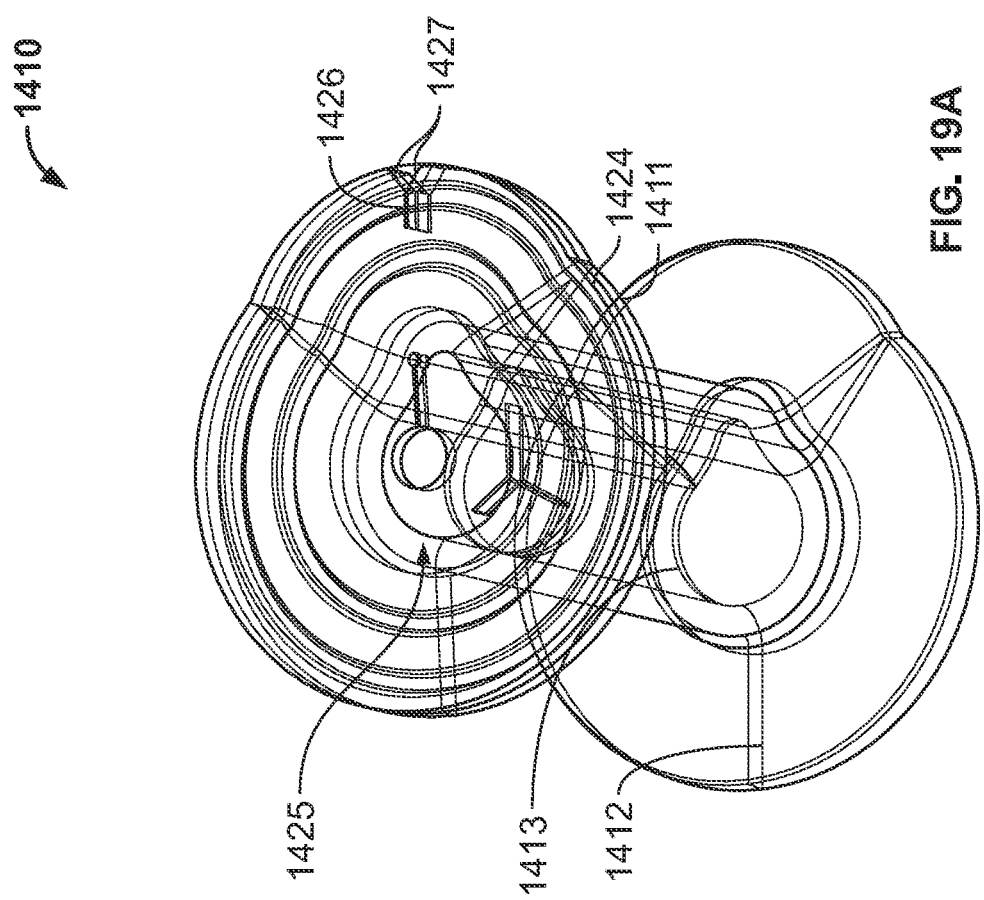
FIG. 19A is a perspective view of a cannula with a split flange according to another embodiment of the invention.

In still further embodiments of the invention, FIGS. 19A-B depicts central passageway 1413, distal flange 1412, primary portion 1421, and first diaphragm 1425, as described above. In this embodiment, split 1426 and split faces 1427 extends through both layer 1424 and proximal flange 1411 along a portion of secondary portion 1422. In this manner, a suture may be parked within split 1426. For instance, a suture may extend from diaphragm 1425, over the flange and layer (if present), and into split 1426. Split faces 1427 allow for greater access to split 1426 such that a surgeon is not required to precisely place a suture within split 1426 to park the suture.

Although FIGS. 19A-B depicts split 1426 and split faces 1427 extending through layer 1424 and proximal flange 1411, it is envisioned that, in other embodiments, the split and split faces may extend only into one or the other of the layer or proximal flange. In yet another embodiment, there may be no layer, and thus the split and split faces may only be on the proximal flange. In yet another embodiment, split faces may be non-linear (e.g. round, jagged, or the like). In yet another embodiment, the split may be non-linear (e.g. curved, angled, "L" shaped, zig-zagged, or any other shape known to one skilled in the art). In yet another embodiment, while in FIGS. 19A-B the split is shown in the secondary portion of the irregular shape, the split and split faces may instead be located elsewhere on the flange, such as on a portion of the primary portion. In yet another embodiment, the split may extend from the secondary portion into the primary portion. In yet another embodiment, there may be a void at a tip of the split.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for positioning a cannula comprising:
engaging an inserter with the cannula, the cannula having a flexible body including a central passageway bounded by a first flange and a second flange, the second flange having an irregular shape, the inserter directly engaged with the second flange to reconfigure the second flange from a first position having a first radial dimension to a second position having a second radial dimension less than the first radial dimension;
passing at least the second flange of the cannula and the inserter into a surgical opening formed in a patient through at least one layer of tissue;
moving the second flange and the inserter through the at least one layer of tissue such that at least a portion of the second flange is located under the layer of tissue;
releasing the inserter from the second flange; and
removing the inserter from the surgical opening.

2. The method of claim 1, wherein the cannula is monolithic.

3. The method of claim 1, wherein the cannula includes a first diaphragm positioned therein, the first diaphragm including at least a first diaphragm slit, the method further comprising positioning a suture through the central passageway of the cannula and moving the suture radially to pass the suture through the first diaphragm slit to maintain the suture in a radial position.

4. The method of claim 3, wherein the cannula includes a second diaphragm positioned adjacent to or at one of the first or second flanges and having at least one second diaphragm slit, the step of moving the suture radially including passing the suture through the second diaphragm slit to maintain the suture in the radial position.

5. The method of claim 1, wherein after releasing the inserter from the second flange, the second flange biases outwards from the inserter.

6. The method of claim 1, wherein after releasing the inserter from the second flange, the second flange returns to the first position.

7. The method of claim 1, wherein the cannula has a longitudinal axis extending along the central passageway and through the first and second flanges, and engaging the inserter with the cannula includes positioning the inserter through an opening towards the second flange to engage the inserter with the second flange and rotating the inserter relative to the cannula to twist the cannula around the longitudinal axis.

8. The method of claim 1, wherein moving the second flange and the inserter through the at least one layer of tissue includes flexing corners of the second flange inward to pass an interior tissue wall of the at least one layer of tissue and biasing the corners outward from the inserter to inhibit removal back through the at least one layer of tissue.

9. The method of claim 1, wherein the second flange includes a separation along a perimeter of the second flange, the separation forming a first end and a second end.

10. The method of claim 9, wherein at least a portion of the first and second ends overlap to form a watertight seal at the second flange.

11. The method of claim 9, wherein engaging the inserter with the cannula includes positioning the inserter through the central passageway and engaging one of the first and second ends of the separation.

12. The method of claim 11, further comprising holding the first flange stationary and rotating the inserter in a first direction relative to the first flange such that the cannula twists around itself and transitions from an untwisted shape to a twisted shape prior to the passing step.

13. The method of claim 12, further comprising using the second flange as tactile feedback to determine the correct positioning of the cannula when the cannula is in the twisted shape.

14. The method of claim 12, further comprising rotating the inserter in a second direction opposite the first direction to revert the cannula from the twisted shape to the untwisted shape.

15. The method of claim 9, wherein the first end includes a first flap and the second end includes a second flap, the first flap configured to seal the second flange at the separation, and the step of engaging the inserter with the cannula includes engaging the inserter with the second flap.

16. The method of claim 9, wherein engaging the inserter with the cannula includes engaging the inserter with a tab extending from at least one of the first and second ends to provide a more stable engagement between the inserter and the cannula.

17. The method of claim 1, further comprising after releasing the inserter from the second flange and prior to removing the inserter, adjusting the cannula to obtain proper compression of an interior tissue wall to expand joint space or proper orientation of the central passageway.

18. The method of claim 1, further comprising removing the cannula by:
positioning the inserter within the central passageway;
engaging the second flange while holding the first flange stationary;
rotating the inserter to twist the cannula into a twisted, tapered shape; and
removing the cannula from the surgical opening.

19. The method of claim 1, wherein engaging the inserter with the cannula includes positioning the inserter through the central passageway of the cannula and folding the second flange to insert a distal tip of the inserter into a hole of the second flange.

20. A method for positioning a cannula comprising:
engaging an inserter with the cannula, the cannula having a flexible body including a central passageway bounded by a first flange and a second flange, wherein the cannula is in an untwisted position and engaging the inserter with the cannula includes engaging the inserter with the second flange;
rotating the inserter to twist the second flange relative to the first flange to reconfigure the cannula from the untwisted position to a twisted position;
passing at least the second flange of the cannula and the inserter into a surgical opening formed in a patient through at least one layer of tissue;

moving the second flange and the inserter through the at least one layer of tissue;
releasing the inserter from the second flange; and
removing the inserter from the surgical opening.

* * * * *